(12) United States Patent
Yan et al.

(10) Patent No.: US 6,379,712 B1
(45) Date of Patent: Apr. 30, 2002

(54) NANOSILVER-CONTAINING ANTIBACTERIAL AND ANTIFUNGAL GRANULES AND METHODS FOR PREPARING AND USING THE SAME

(75) Inventors: Jixiong Yan, Wuhan; Jiachong Cheng, Beijing, both of (CN)

(73) Assignee: GloboAsia, L.L.C., Hanover, MD (US)

( * ) Notice: Subject to any disclaimer, the term of this patent is extended or adjusted under 35 U.S.C. 154(b) by 0 days.

(21) Appl. No.: 09/840,906

(22) Filed: Apr. 25, 2001

Related U.S. Application Data
(60) Provisional application No. 60/230,925, filed on Sep. 13, 2000.

(51) Int. Cl.[7] .......................... A01N 59/16; A61K 9/24; A61N 25/00
(52) U.S. Cl. .................. 424/618; 424/484; 424/488; 514/770
(58) Field of Search ................................ 424/484, 488, 424/618; 514/770

(56) References Cited

U.S. PATENT DOCUMENTS

| | | |
|---|---|---|
| 4,828,832 A | 5/1989 | De Cuellar et al. |
| 5,709,870 A | 1/1998 | Yoshimura et al. |
| 5,785,972 A | 7/1998 | Tyler |
| 5,824,267 A | 10/1998 | Kawasumi et al. |
| 5,973,050 A | 10/1999 | Johnson et al. |

*Primary Examiner*—Jon P. Weber
*Assistant Examiner*—Kailash C. Srivastava
(74) *Attorney, Agent, or Firm*—Fei-Fei Chao; Venable, Baetjer, Howard & Civiletti

(57) ABSTRACT

The present invention relates to nanosilver-containing antibacterial and antifungal granules ("NAGs"). The NAGs have longlasting inhibitory effect on a broad-spectrum of bacteria and fungi, which include, but are not limited to, *Escherichia coli*, Methicillin resistant *Staphylococcus aureus, Chlamydia trachomatis, Providencia stuartii, Vibrio vulnificus*, Pneumobacillus, Nitrate-negative bacillus, *Staphylococcus aureus, Candida albicans, Bacillus cloacae, Bacillus allantoides*, Morgan's bacillus (*Salmonella morgani*), *Pseudomonas maltophila, Pseudomonas aeruginosa, Neisseria gonorrhoeae, Bacillus subtilis, Bacillus foecalis alkaligenes, Streptococcus hemolyticus* B, Citrobacter, and *Salmonella paratyphi* C. The NAGs contain ground stalk marrow of the plant *Juncus effusus* L. which has been dispersed with nanosilver particles. The nanosilver particles are about 1–100 nm in diameter. Each of the nanosilver particles contain a metallic silver core which is surrounded by silver oxide. The present invention also provides a process for making the NAGs. The NAGs can be used in a variety of healthcare and industrial products. Examples of the healthcare products include, but are not limited to, ointments or lotions to treat skin trauma, soaking solutions or cleansing solutions for dental or women hygiene, medications for treating gastrointestinal bacteria infections, sexual related diseases, and eye diseases. Examples of industrial products include, but are not limited to, food preservatives, water disinfectants, paper disinfectants, construction filling materials (to prevent mold formation).

7 Claims, 2 Drawing Sheets

NANOSILVER-CONTAINING ANTIBACTERIAL AND ANTIFUNGAL GRANULES AND METHODS FOR PREPARING AND USING THE SAME

RELATED APPLICATION

This application claims the priority of U.S. Provisional Application No. 60/230,925, filed on Sep. 13, 2000, which is herein incorporated by reference.

FIELD OF THE INVENTION

The present invention relates to nanosilver particles-containing antibacterial and antifungal granules (NAGs). The nanosilver particles are attached to the surfaces and pores of stalk marrow of *Juncus effusus* L, which acts as an inert carrier for nanosilver. Each of the nanosilver particles contains a metallic silver core which is surrounded by silver oxide. The size of the nanosilver particle is between 1–100 nm in diameter. The present invention also relates to methods for preparing the NAGs and for using the NAGs. The NAGs can be used in a variety of healthcare, medicinal and industrial products.

DESCRIPTION OF THE RELATED ART

Metals including silver, copper, mercury, and zinc are known for anti-bacterial properties. Bacteria treated by these metals do not acquire resistance to the metals. Therefore, the bactericidal metals have advantages over the conventional antibiotics which often cause the selection of antibiotic-resistant microorganism.

Silver is generally a safe and effective antimicrobial metal. Silver ions function in adversely affecting cellular metabolism to inhibit bacterial cell growth. When silver ions are absorbed into bacterial cells, silver ions suppress respiration, basal metabolism of the electron transfer system, and transport of substrate in the microbial cell membrane. Silver ions also inhibit bacterial growth by producing active oxygen on the surface of silver powder and silver-plated articles. Silver has been studied for antibacterial purposes in the form of powder, metal-substituted zeolite, metal-plated non-woven fabric, and crosslinked compound.

U.S. Pat. No. 5,785,972 discloses a therapeutically active composition comprising a solution of colloidal silver, helichrysum angustifolium or helichrysum italicum oil, and raw honey emulsified with water soluble lecithin. However, the contact between microbial cells and silver ions is not ensured as the silver ions quickly become eluted in the solution. Silver ions in solution are difficult to handle and therefore of limited use.

To solve the problem in liquid state, various crosslinked agents and solid supports for silver ions have been developed. For example, U.S. Pat. No. 5,709,870 discloses a silver-containing antimicrobial agent comprising a silver salt of carboxymethylcellulose and having a degree of substitution of carboxymethyl group of not less than 0.4.

Chinese Patent No. 87100231A discloses an antibacterial dressing made from nitrilon crosslinked with copper salts in alkaline medium. The resulted cloth shows antibacterial activity on ten (10) bacteria including *Staphylococcus aureus* (MRSA).

Japan Process Technique, Vol. 17, No. 7, teaches a nitrilon fiber manufactured from copper and sulfur salts. The fiber has bacteriostatic effects on *Escherichia coli, Staphylococcus aureus, Bacillus subtilis*, and Epidermophyton.

Japanese Patent No. 3-136649 discloses an anti-bacterial cloth used for washing breasts of milk cow. The $Ag^+$ ions in $AgNO_3$ were crosslinked with polyacrylonitrile and it had anti-bacterial activity on six (6) bacteria including Streptococcus and Staphylococcus.

Japanese Patent No. 54-151669 discloses a fiber treated with a solution of a compound of copper and silver. The solution is evenly distributed on the fiber. The fiber is used as an anti-bacterial lining inside boots, shoes, and pants.

U.S. Pat. No. 4,828,832 discloses a composition for treating skin lesions which is made up of metallic silver particles having a diameter of 1 to 10 µm and an optional oxidizing agent randomly disbursed within a carrier of inert filler such as kaolin or talc.

U.S. Pat. No. 5,824,267 discloses a plastic material having a bactericidal surface on which a number of ceramic or base metal particles of a mean diameter of 0.01 to 0.5 µm are embedded under the condition that a portion of each particle is exposed over the surface, and the ceramic or base metal particles have bactericidal metal particles of mean diameter of 0.0001 to 0.1 µm dispersively fixed thereon.

Such solid supports using synthetic polymer materials have been not widely adapted for medical and healthcare purposes. These materials usually require bonding or crosslinking of the silver or silver ions to the polymers. Such bonding or cross-linking may invoke allergic reactions in patients. These materials also do not have sufficiently high antibacterial activity due to the lack of sufficient surface contact with the bacteria. Additionally, the bactericidal activity of these materials rapidly diminishes as the silver ions become separated from the solid supports, thus, these materials do not show bactericidal activity over a prolonged period of time. Lastly, the processes for making these materials are complicated and time-consuming.

The present invention provides nanosilver-containing antibacterial and antifungal granules (NAGs). The NAGs are made of stalk marrow of *Juncus effusus* L. (as a carrier) with nanosilver particles evenly dispersed on the surfaces and pores of the stalk marrow. These NAGs display longlasting bactericidal and fungicidal activities. The NAGs of the present invention are safe to use for medical and healthcare purposes as well as used in industrial products.

The present invention also provides a method for making the NAG which is suitable and feasible for large scale industrial production. The present invention is an improvement over Chinese Patent Nos. CN 1034090, CN 1093004, and CN 1123665, which are herein incorporated by reference. CN 1034090 discloses a method of attaching nanosilver particles to textile. CN 1093004 discloses a suture or medical thread containing nanosilver particles. CN 1123665 discloses a granule containing nanosilver particles attached to stalk marrow which can be used to disinfect tooth brush, for treatment of acne and pimples, and as cleansing agents to prevent gynecological infections such as vaginitis. The method for making the NAGs and the utility of using the NAGs described in the present invention are different from those described in CN 1034090, CN 1093004, and CN 1123665.

SUMMARY OF THE INVENTION

The present invention provides nanosilver-containing antibacterial and antifungal granules (NAGs) which comprise nanosilver particles which are firmly and evenly attached to stalk marrow of *Juncus effusus* L. The nanosilver particles are about 1–100 nm in diameter. The individual nanosilver particle has a metallic silver core surrounded by silver oxide.

The NAGs display longstanding inhibitory effect on a broad spectrum of bacteria and fungi. Examples of the bacteria and fungi include, but are not limited to, *Escherichia coli*, Methicillin resistant *Staphylococcus aureus*, *Chlamydia trachomatis, Providencia stuartii, Vibrio vulnificus*, Pneumobacillus, Nitrate-negative bacillus, *Staphylococcus aureus, Candida albicans, Bacillus cloacae, Bacillus allantoides*, Morgan's bacillus (*Salmonella morgani*), *Pseudomonas maltophila, Pseudomonas aeruginosa, Neisseria gonorrhoeae, Bacillus subtilis, Bacillus foecalis alkaligenes, Streptococcus hemolyticus* B, Citrobacter, and *Salmonella paratyphi* C.

The NAGs are produced by (1) cutting the stalk marrow of *Junicus effusus* L. into pieces; (2) immersing the cut stalk marrow in a solution containing nanosilver particles to allow the attachment of the nanosilver particles to the cut stalk marrow; (3) after the attachment, drying the nanosilver particles-attached stalk marrow; and (4) grinding the nanosilver particles-containing stalk marrow to appropriate size to produce the NAGs. Before drying the nanosilver particles-containing stalk marrow, the stalk marrow is optionally washed with hot and cold water.

The nanosilver particles are made by dissolving silver nitrate in a solution containing concentrated ammonia water, glucose or ascorbic acid (as reducing agent), and an oxidizing agent. Optionally, NaOH can be added to the solution to adjust the pH, and ethanol can be added to the solution to improve the solubility of the solution. The preferred oxidizing agent is hydrogen peroxide ($H_2O_2$).

The present invention also provides a method for preparing the NAGs. The method comprises the following steps: (1) cutting the stalk marrow of *Junicus effusus* L. into pieces (about 0.5 to 2 cm at length); (2) preparing a nanosilver particles-containing solution; (3) immersing and thoroughly mixing the cut stalk marrow pieces in the nanosilver particles-containing solution to allow the attachment of the nanosilver particles to the cut stalk marrow pieces; (4) washing the cut stalk marrow pieces (preferably first with hot water, then with cold water); (5) drying the cut stalk marrow pieces; and (6) grinding the dried cut stalk marrow pieces to the desirable size(s) of the NAGs. It is preferred that the NAGs have a size which is capable of passing through a No. 200 sieve. It is preferred to boil the cut stalk marrow pieces to remove unwanted water-soluble materials, followed by heat drying the boiled stalk marrow pieces, before soaking the stalk marrow pieces in the nanosilver particle-containing solution. It is also preferred to treat the nanosilver soaked stalk marrow pieces with heat until the stalk marrow pieces turn brown, before washing the stalk marrow pieces with hot and cold water.

The nanosilver solution is prepared by the following step-wise procedure: (1) dissolving silver nitrate ($AgNO_3$) crystal in a concentrated ammonia water solution; (2) adding glucose or ascorbic acid (as reducing agent) to the solution; and (3) adding an oxidizing agent to the solution. The preferred oxidizing agent is hydrogen peroxide ($H_2O_2$). Optionally, NaOH and ethanol can be added to the nanosilver solution to adjust the pH and improve the solubility of the nanosilver solution, respectively.

Additionally, the present invention provides methods of using the NAGs. The NAGs can be used in a variety of healthcare, medicinal, and industrial products. The NAGs can be added to ointments, lotions, and/or solutions for treating humans or animals with skin trauma, such as acne or pimples, wound, burns, skin with bacterial or fungal infections. In addition, the NAGs can be used in hygiene products, such as women gynecological washing solution, tooth brush soaking solution, or facial cleansing solution.

The NAGs can also be used as food preservatives (e.g., for preserving fruits and vegetables), water disinfectants, paper disinfectants (e.g., for preventing mold build-up in book, newspaper, certificate, envelope, stationary, money, paper food containers, etc.), and in construction filling materials to prevent mold formation. Finally, the NAGs can be used as medicines to treat patients with gastrointestinal infection, sexually transmitted diseases, and eye diseases.

DETAILED DESCRIPTION OF THE INVENTION

Figure 1:
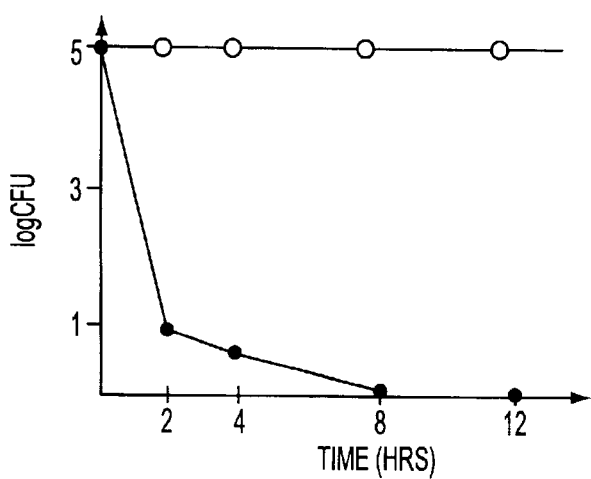
FIG. 1 shows the inhibitory effect of the NAGs on *Staphylococcus. aureus*. The horizontal axis of the curve is the treatment time, the vertical axis is the amount of the bacteria remained (measured by CFU (colony forming units)) after being immersed in the NAGs-containing solution. Open circle indicates no NAGs. Close circle indicates with NAGs.

The present invention is directed to sustained-effect, broad-spectrum nanosilver-containing antibacterial and antifungal granules (NAGs) and the process of manufacturing and using NAGs. The NAGs of the present invention are made by attaching nanosilver particles to small pieces of stalk marrow of the plant *Juncus effusus* L. The attachment of nanosilver particles to the NAGs have been confirmed by scanning electromicroscopy using AMRAY1910FE and TN-8502, which shows that the nanosilver particles on the NAGs were about 25 nm in diameter. The nanosilver particles were shown evenly distributed on the NAGs. The content of the nanosilver particles in the NAGs were analyzed by silver titrimetric method (see infra) to contain about 20–100 mg of silver per g of the NAGs. Also, due to the fact that the surface of the nanosilver particles was dark brown, which is a characteristic of silver oxidation, the surface of the nanosilver particles were identified to be silver oxide.

Juncus or rush pith, "Deng Xin Cao" in Chinese, has the pharmaceutical name Medulla *Junici effusi*, botanical name *Juncus effusus* L. var. decipiens Buchen. The plant belongs to the family of Juncaceae and is grown in the provinces of Jiangsu, Sichuan, Yunnan, and Guizhou in China. Juncus is harvested at the end of summer through autumn. There is no known major active ingredients in the plant. Because of its inert characteristics, the stalk marrow of Juncus is suitable for use as a carrier for nanosilver particles.

The NAGs of the present invention have demonstrated high antibacterial and antifungal effects. They are also non-toxic, non-stimulative, and non-allergic, so that they can be safely used in a large variety of healthcare, medicinal, and industrial products.

The antibactial and antifungal effects of the NAGs can be explained in the following four (4) chemical process:

(1) AgNO3+reducing agent (Glucose or Ascorbic Acid) →Ag;

(2) Ag+$O_2$ (oxidizing agent)→$Ag_2O$;

(3) $Ag_2O_{(at\ the\ surface\ of\ the\ particles)}$+$H_2O$→$2Ag^+$+$2OH^-$;

(4)

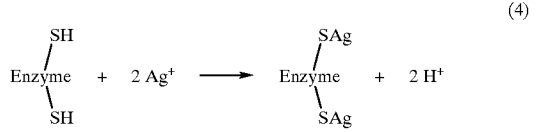

Silver ion is an effective antiseptic and germicide, and its organic salts, particularly in the form of nitrates, are commonly used with farazolidones and antibiotics in the treatment of burns. Silver nitrate is one of the most powerful chemical germicides and is widely used as a local astringent and germicide. However, the nitrates irritate the skin. Thus, it is preferable to reduce the silver nitrate to metallic silver in the first (1) reaction. The metallic silver, as demonstrated in the second (2) reaction, is then undergone an oxidation to produce silver oxide ($Ag_2O$) in the presence of an oxidizing agent. When silver oxide is interacted with water, as shown in the third (3) reaction, it undergoes ionization to produce silver ion ($Ag^+$). Finally, as shown in the fourth reaction (4), when the silver ion interacts with the sulfhydryl group (—SH) of an enzyme, it forms a —SAg linkage, which effectively blocks the enzyme activity. Therefore, the antibacterial and antifungal activity of the NAGs appears to be even more prominent when the NAGs are in contact with water.

The NAGs has a broad spectrum of antibacterial and antifungal activity. The NAGs of the present invention had bactericidal and fungicidal effects on more than twenty (20) common pathogens, which include, but are not limited to, *Escherichia coli*, Methicillin resistant *Staphylococcus aureus*, *Chlamydia trachomatis*, *Providencia stuartii*, *Vibrio vulnificus*, Pneumobacillus, Nitrate-negative bacillus, *Staphylococcus aureus*, *Candida albicans*, *Bacillus cloacae*, *Bacillus allantoides*, Morgan's bacillus (*Salmonella morgani*), *Pseudomonas altophila*, Arizona, *Pseudomonas aeruginosa*, *Neisseria gonorrhoeae*, *Bacillus subtilis*, *Bacillus foecalis alkaligenes*, *Streptococcus hemolyticus* B, Citrobacter, *Salmonella paratyphi* C.

Figure 2:
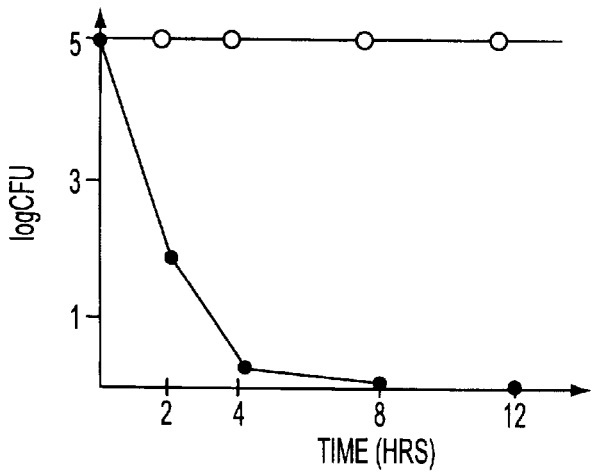
FIG. 2 shows the inhibitory effect of the NAGs on *Escherichia coli*. The horizontal axis of the curve is the treatment time, the vertical axis is the amount of the bacteria remained (measured by CFU (colony forming units)) after being immersed in the NAGs-containing solution. Open circle indicates no NAGs. Close circle indicates with NAGs.
Figure 3:
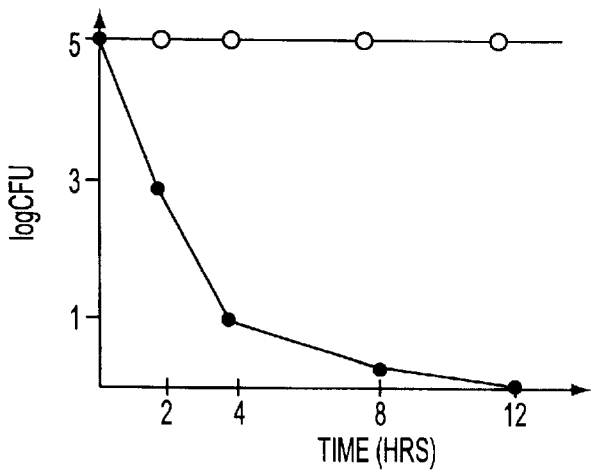
FIG. 3 shows the inhibitory effect of the NAGs on *Pseudomonas aeruginosa*. The horizontal axis of the curve is the treatment time, the vertical axis is the amount of the bacteria remained (measured by CFU (colony forming units)) after being immersed in the NAGs-containing solution. Open circle indicates no NAGs. Close circle indicates with NAGs.

Examples of the antibacterial activity of the NAGs were demonstrated in FIGS. 1–3. FIG. 1 shows the effect of the NAGs on *Staphylococcus aureus*. The data demonstrate that within 8 hours of treatment with the NAGs, all of the *S. aureus* were killed. FIG. 2 shows the effect of the NAGs on *Escherichia coli*. The data also demonstrate that within 8 hours of treatment with the NAGs, all of the *E. coli* were killed. FIG. 3 shows the effect of the NAGs on *Pseudomonas aeruginosa*. The data show that within 12 hours of treatment with the NAGs, all of the *P. aeruginosa* were killed.

The NAGs were prepared by first cutting the stalk marrow of *Juncus effusus* L. into pieces of 0.5 to 2 cm at length. These small pieces of stalk marrow were washed, followed by boiling in water to remove any unwanted water soluble materials. The boiled stalk marrow pieces were than dried for later use. In the meantime, a nanosilver particles-containing solution was prepared by first dissolving $AgNO_3$ in ammonia water, followed by adding glucose (as reducing agent) to the reaction solution. An oxidizing agent, preferably $H_2O_2$, was then added to the reaction solution. The quantity or volume of each of the ingredients used in the nanosilver particle-containing solution is listed in Table 1.

TABLE 1

| The Nanosilver Particles-Containing Solution | |
|---|---|
| Ingredients | Quantity or Volume |
| $AgNO_3$ | 15 Kg |
| Ammonia Water | 15 L |
| Glucose | 3 Kg |
| Ethanol (95%) | 5 L |
| NaOH | 0.5 Kg |
| Oxidizing Agent (e.g., $H_2O_2$) | 100 ml |
| Distilled Water | up to 1000 L |

The above quantity of the nanosilver particles-containing solution was aimed at large scale industrial manufacturing use. The quantity could be scaled down proportionally for research and laboratory testing.

Figure 4:
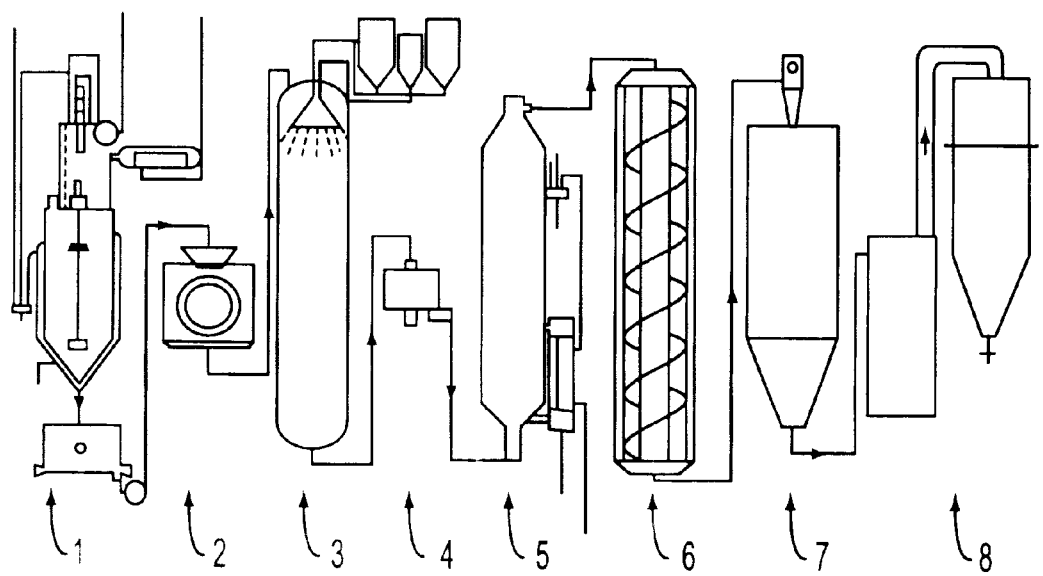
FIG. 4 is a flow chart indicating the process for making the NAGs in an industrial scale manufacturing. There are eight (8) chambers associated with the process, which are: (1) selection chamber; (2) separation chamber; (3) spraying chamber; (4) water removal chamber; (5) heat reaction chamber; (6) washing and soaking chamber; (7) drying chamber; and (8) grinding chamber. The function of each chamber will be described in the following section (infra).

FIG. 4 shows a flow chart of industrial production of the NAGs. The process was operated in the following chambers: (1) selection chamber; (2) separation chamber; (3) spraying chamber; (4) water removal chamber; (5) heat reaction chamber; (6) washing and soaking chamber; (7) drying chamber; and (8) grinding chamber.

As shown in FIG. 4, in the "selection" chamber, stalk marrow of *Juncus effusus* L. were cut into pieces, preferably at a length of about 0.5 to 2 cm. The small pieces of stalk marrow were sieved through a selection process and transferred to the "separation" chamber, where the stalk marrow pieces were boiled and dried. The small pieces of dried stalk marrow were then transferred to the "spraying" chamber where the nanosilver particles-containing solution was evenly sprayed and dispersed onto the small pieces of dried stalk marrow. The small pieces of stalk marrow were further soaked with the nanosilver particles-containing solution in the "spraying" chamber for an adequate amount of time. The small pieces of stalk marrow with attached nanosilver particles were then transferred to the "water removal" chamber where excess solution was removed from the pieces.

The small pieces of stalk marrow were then transferred to the "heat reaction" chamber, where the nanosilver-attached stalk marrow pieces were treated with heat.

The heat-reacted stalk marrow pieces were transferred to the "soaking and washing" chamber, where the pieces were soaked and washed first with hot water, then with cold water, to remove any unattached nanosilver particles and water-soluble substances. The washed nanosilver particles-attached stalk marrow pieces were then dried under heat in the "drying" chamber, and finally transferred to the "grinding" chamber to be ground to proper NAG sizes. The final NAGs should contain no water-soluble substances other than silver. These NAGs could be used in various healthcare, medicinal and industrial products to disinfect, inhibit the growth of bacteria or fungi, and/or prevent mold formation.

Examples of the NAGs used in healthcare products include, but are not limited to, ointments, lotions, or spraying solutions for treating all kinds of injuries and/or burns, bacterial and fungal infections (including gynecological infections such as vaginitis), cleansing agents for clothing, women hygiene, acne or pimples, and soaking solution for tooth brush. Examples of the NAGs used in medicinal products include, but are not limited to, internal medicines for treating gastrointestinal bacterial infection, sexually transmitted diseases, or as an eye drop for treating eye diseases. Examples of the NAGs used in industrial products include, but are not limited to, food preservatives especially for fruits and vegetables, drinking water disinfectants, paper and construction filling materials preservation (especially to prevent mold formation).

The following examples are illustrative, but not limiting the scope of the present invention. Reasonable variations, such as those occur to reasonable artisan, can be made herein without departing from the scope of the present invention.

EXAMPLE 1

Titrimetric Analysis of Silver in NAGs

The content of the silver in the NAGs was analyzed by a titrimetric analysis as follows:

A. Basic Chemical Reactions

The basic chemical reactions involved in the volumetric analysis were:

$$Ag^+ + SCN^- \rightarrow AgSCN \downarrow$$

$$Fe^{+3} + 6SCN^- \rightarrow Fe(SCN)_6^{-3}{}_{(light\ brownish\ red)}\text{ (end point)}$$

B. Preparation of Solutions (1). Solvent:

$HNO_3$ solution. The solution was prepared by mixing nitric acid with water at ratio 1:1 (v/v). The concentration of nitric acid in the solution was 6N.

(2). Indicator:

10% $NH_4Fe(SO_4)_2$ aqueous solution (w/v).

(3). Titrant:

$NH_4SCN$ standardized solution.

0.75 g $NH_4SCN$ was weighed and dissolved in 1000 ml water in a volumetric flask. The flask was gently shaken to evenly distribute $NH_4SCN$ in the solution. The solution was standardized by a standard Ag solution.

(4). Standard Ag solution:

1.0000 g of clean and dry silver shreds or flakes was weighed and cut into small pieces. The pieces were placed in a 1000 ml brown volumetric flask and completely dissolved in 100 ml 6N $HNO_3$ by heat in water bath. The flask was covered with filter paper during the heating process. After the flask cooled down, the volume of solution was brought up to 1000 ml by water. The flask was shaken to disperse the solute. The final concentration of the solution was 1 mg/ml.

C. Standardizing $NH_4SCN$ Solution

Ten (10) ml of standard Ag solution (1 mg/ml) as shown in B(4) was measured and poured into a 200 ml volumetric flask. For the blank control, 10 ml of water was poured into the 200 ml volumetric flask. Then, 6N $HNO_3$ was added to the flask (the acidic level of nitric acid was between 1–10%), followed by adding 1–2 ml of 10% $NH_4Fe(SO_4)_2$ aqueous solution to the flask as the indicator. Water was then added along the wall of the flask until the volume was kept at 80–100 ml. $NH_4SCN$ solution prepared in B(3) was used as titrant to react with silver solution until a stable light brownish red appeared, which signaled the end of the reaction. The titrimetric analysis was conducted in triplicates to get a mean value. The standard deviation (SD) of the mean values should be less than 0.10 ml. The silver titer value, $T_{Ag}$, was calculated:

$T_{Ag}$=Ag amount in Ag standard solution/[(mean volume of the triplicates)−blank] (The unit for $T_{Ag}$ is mg/ml.)

D. Titrimetric Analysis of the NAGs 100.0 mg of the NAGs, after being dried in a desiccator for 2 to 4 hours, was precisely measured and placed in a 200 ml flask. Then, 20–30 ml of 6N $HNO_3$ were added into the flask, and the flask was placed on a low-heat thermoelectrical plate until the solution was slightly boiling, where the solution was maintained at this stage until the solution became colorless. Then, the flask was cooled down and diluted to 100 ml. 1–2 ml indicator was added to the solution. The solution was analyzed by titration using the standardized $NH_4SCN$ solution. When the solution was stable in a color of light brownish red, it was the end point of the titration.

E. Results

The content of the silver in the NAGs was calculated by the following equation.

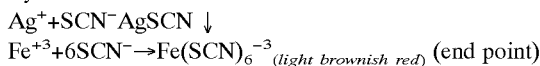

Ag% in the NAGs=$(V \times T_{Ag}/W) \times 100\%$

Where V was the volume of the $NH_4SCN$ solution added to the titration flask after the blank was deducted. $T_{Ag}$ was in the unit of mg Ag/ml. W was the weight of the NAG sample in mg.

From the above calculation, the silver content of the NAGs was about 2–8%.

EXAMPLE 2

Antibacterial Effect of the Solution Containing the NAGs

The antibacterial effect of the NAGs in the solution was tested as follows:

A. Preparation of the NAGs Solution

Five (5) g of the NAGs were suspended in 500 ml of water and stayed in the solution for 24 hrs to obtain an NAGs-containing solution.

B. Preparation of Bacteria

M-H liquid and solid culture media were used for activation and culture of the bacteria.

*Staphylococcus aureus* stock M120, *Escherichia coli* stock E109, and *Pseudomonas aeruginosa* stock PS208 were used for the testing. These stocks were provided by the Microbiology Teaching and Research Section at Henan Medical University.

The frozen stocks of bacteria were seeded onto solid culture media. Single colonies were picked and inoculated respectively in 2 ml liquid culture medium and cultured at 37° C. for eight (8) hours. Then, the liquid culture medium was diluted at 1:1000 and stored in refrigerator (around 0° C.) until ready for use. The solution contained about $10^5$ CFU/ml bacterial stock.

C. Treatment of Bacterial Stocks in the Solution

Under sterile condition, the NAGs-containing solution was added to three (3) flasks, each containing 100 ml of the solution. One (1) ml of the bacterial stocks of *E. coli, S. aureus*, or *P. aeruginosa* was then added to the three flasks, respectively. The control was prepared by adding the bacterial stocks in the flasks containing water. The inhibitory effect of the NAGs on the three different bacteria was conducted over a period of eight (8) hours.

D. Results of the Experiment

At the end of the eight hours study, the solution was diluted and plated on a culture plate to measure the number of remaining bacteria. In the solution containing the NAGs, more than 99% of all the tested bacteria were killed, which demonstrated that the NAGs-containing solution was very effective as bactericide and could be used as disinfectant.

EXAMPLE 3

Time Course of Antibacterial Effects of the NAGs

A time course study of the antibacterial effects of the NAGs in a solution was conducted as follows:

A. Preparation of Bacterial Stocks

M-H liquid and solid culture media were used for activation and culture of the bacteria. *Staphylococcus aureus* stock M120, *Escherichia coli* stock E109, and *Pseudomonas aeruginosa* stock PS208 were provided by the Microbiology Teaching and Research Section at Henan Medical University. The stocks were cultured in an incubator at 37° C. for 24 hours.

The frozen stocks of bacteria were seeded to a culture plate. Single colonies were chosen and inoculated in 2 ml liquid culture medium, respectively, where they were cultured at 37° C. for eight (8) hours. Then, the liquid culture medium was diluted at 1:1000 and stored in the refrigerator (around 0° C.) until ready for use. The solution contained about $10^5$ CFU/ml bacterial stock.

B. The Effect of the NAGs on *E. coli*, *S. aureus*, and *P. aeruzinosa*

Under sterile condition, three (3) flasks, which contained 100 ml of the NAGs-containing solution in each flask, were inoculated with *E. coli*, *S. aureus*, or *P. aeruginosa*, respectively, with about $10^4$–$10^5$ bacteria per ml in the solution. A time course was studied at 2, 4, 8, 12, and 24 hours intervals, each with 0.5 ml of sample. The viable number of the bacteria was counted. The control study was conducted with the same number of bacteria incubated at the same condition in a 100 ml of water rather than the NAGs-containing solution.

C. Results

As shown in FIG. 1, after inoculating *S. aureus* in a solution containing the NAGs, the number of *S. aureus* reduced to 0.01% of the starting number during the first two hours after the inoculation. Eight (8) hours after the inoculation, all of the bacteria were killed.

As shown in FIG. 2, after inoculating *E. coli* in a solution containing the NAGs, the number of *E. coli* reduced to 0.1% of the starting number during the first two hours after the inoculation. Eight (8) hours after the inoculation, all of the bacteria were killed.

As shown in FIG. 3, after inoculating *P. aeruginosai* in a solution containing the NAGs, the number of *E. coli* reduced to 1% of the starting number during the first two hours after the inoculation. Twelve (12) hours after the inoculation, all of the bacteria were killed The results of this study indicate that the NAGs had inhibitory effects on *E. coli*, *S. aureus*, and *P. aeruginosa*.

EXAMPLE 4

Antibacterial Effect of the NAGs on Toothbrush

The antibacterial effect of the NAGs was tested on toothbrush as follows:

A. Preparation of Bacteria

M-H liquid and solid culture media were used for activation and culture of the bacteria. *Staphylococcus aureus* stock M120 was provided by the Microbiology Teaching and Research Section at Henan Medical University. The stock was cultured in an incubator at 37° C. for 24 hours.

The frozen stock of bacteria was seeded to a culture plate. A single colony was chosen and inoculated in 2 ml liquid culture medium, respectively, where the bacteria were cultured at 37° C. for eight (8) hours. Then, the liquid culture medium was diluted at 1:1000 and stored in the refrigerator (around 0° C.) until ready for use. The solution contained about $10^5$ CFU/ml bacterial stock.

B. Treatment of Toothbrush

The bactericidal activity of the NAGs on toothbrush was tested by two (2) methods:

(1). Treatment of Toothbrush in its Natural State

A half of a toothbrush was immersed in 30 ml of a solution containing the NAGs for eight (8) hours. The other half of the toothbrush was immersed in 30 ml of saline solution. One (1) ml of each of the solutions was taken out after the 8 hours incubation, diluted, and tested for bacteria counts on plate. This method tested the natural existence of germs on the toothbrush and the effect of the NAGs on inhibiting the growth of the germs.

(2). Treatment of Toothbrush in Use with Added *Staphylococcus aureus*

A half of the toothbrush was immersed in 30 ml solution containing the NAGs. One (1) ml of the bacterial stock containing *Staphylococcus aureus* was added to the solution. At the end of the 8 hours incubation, 1 ml of the solution was taken out and tested for bacteria counts on plate. The other half of the toothbrush was immersed in 30 ml of saline solution. One (1) ml of each of the solutions was taken out after the 8 hours incubation, diluted, and tested for bacteria counts on plate. This method tested the bactericidal effect of the NAGs on toothbrush where known amount of *S. aureus* was inoculated in the solution.

C. Results (1). Treatment of Toothbrush in its Natural State

The bactericidal efficiency for the NAGs was about 95%.

(2). Treatment of Toothbrush in Use with Added *Staphylococcus aureus*

The bactericidal efficiency for the NAGs was about 98%.

The results show that the NAGs were effective against bacteria which were grown on the toothbrush. Therefore, the NAGs could be effectively used as a disinfectant for toothbrush.

EXAMPLE 5

Testing of the Toxicity of the NAGs on Rats

The NAGs were given to normal, healthy rats in a dose of 925 mg/kg of body weight per day for fourteen (14) days. This dose was more than 4,625 fold of the dose generally recommended to humans. The activities of rats were monitored. At the end of the 14 days period, no rats were dead or sick, which indicated that the NAGs were safe and non-toxic to rats.

EXAMPLE 6

Skin Allergic Test of the NAGs on Rabbits

A 5% (w/v) NAGs-containing solution was applied to the skin of the rabbits. The rabbits were monitored at 1 hr, 24 hrs, and 48 hrs intervals. No rash, bruise, or any irritating reaction was observed on the rabbit skins, which indicated that the NAGs were safe and not creating any allergic reaction on the skins.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

What is claimed is:

1. A nanosilver-containing antibacterial and antifungal granule (NAG) comprising:

nanosilver particles attached to stalk marrow of *Juncus effusus* L.;

wherein each of said nanosilver particles comprises a metallic silver core surrounded by silver oxide.

2. The NAG according to claim 1, wherein said nanosilver particles are 1–100 nm in diameter.

3. The NAG according to claim 1, wherein said NAG inhibits growth of bacteria and fungi, which are ones selected from the group consisting of *Escherichia coli*, Methicillin resistant *Staphylococcus aureus*, *Chlamydia trachomatis*, *Providencia stuartii*, *Vibrio vulnificus*, Pneumobacillus, Nitrate-negative bacillus, *Staphylococcus aureus*, *Candida albicans*, *Bacillus cloacae*, *Bacillus allantoides*, Morgan's bacillus (*Salmonella morgani*), *Pseudomonas maltophila*, *Pseudomonas aeruginosa*, *Neisseria gonorrhoeae*, *Bacillus subtilis*, *Bacillus foecalis alkaligenes*, *Streptococcus hemolyticus* B, Citrobacter, and *Salmonella paratyphi* C.

4. The NAG according to claim 1, wherein said NAG is produced by:

cutting the stalk marrow of *Junicus effusus* L. into pieces;

immersing the cut stalk marrow in a solution containing nanosilver particles to attach the nanosilver particles to the cut stalk marrow;

drying the nanosilver particles-attached stalk marrow; and grinding the nanosilver particles-containing stalk marrow to produce NAG.

5. The NAG according to claim 4, wherein said nanosilver particles-containing solution comprises:

silver nitrate ($AgNO_3$), a concentrated ammonia water solution; glucose or ascorbic acid; and an oxidizing agent.

6. The NAG according to claim 5, wherein said oxidizing agent is hydrogen peroxide ($H_2O_2$).

7. The NAG according to claim 5, further comprising adding ethanol and NaOH to the solution.

* * * * *